C

(12) United States Patent
Udagawa et al.

(10) Patent No.: US 9,173,855 B2
(45) Date of Patent: Nov. 3, 2015

(54) PATCH

(75) Inventors: Hiroko Udagawa, Amagasaki (JP);
Yoshikazu Inaba, Amagasaki (JP);
Yukihiko Noda, Amagasaki (JP); Kumi Obata, Amagasaki (JP); Hiroto Terashima, Amagasaki (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 132 days.

(21) Appl. No.: 13/882,565

(22) PCT Filed: Nov. 2, 2011

(86) PCT No.: PCT/JP2011/075354
§ 371 (c)(1),
(2), (4) Date: Jun. 18, 2013

(87) PCT Pub. No.: WO2012/060431
PCT Pub. Date: May 10, 2012

(65) Prior Publication Data
US 2013/0261572 A1   Oct. 3, 2013

(30) Foreign Application Priority Data
Nov. 2, 2010   (JP) ................................. 2010-246906

(51) Int. Cl.
A61F 13/00   (2006.01)
A61K 31/415   (2006.01)
A61F 13/02   (2006.01)
A61K 9/70   (2006.01)
A61K 31/4168   (2006.01)

(52) U.S. Cl.
CPC ............. *A61K 9/7053* (2013.01); *A61K 9/7023* (2013.01); *A61K 9/7046* (2013.01); *A61K 31/4168* (2013.01)

(58) Field of Classification Search
None
See application file for complete search history.

(56) References Cited

U.S. PATENT DOCUMENTS 3,277,038 A * 10/1966 Wood ............................... 524/71
4,201,211 A   5/1980 Chandrasekaran et al.
4,559,222 A   12/1985 Enscore et al.
5,571,530 A * 11/1996 Nakano et al. ................. 424/448
5,948,433 A   9/1999 Burton et al.
2005/0260255 A1   11/2005 Terahara et al.
2006/0078603 A1   4/2006 Nguyen

FOREIGN PATENT DOCUMENTS

| GB | 2 328 375 | 2/1999 |
| JP | 54-20129 | 2/1979 |
| JP | 59-206307 | 11/1984 |
| JP | 63-203616 | 8/1988 |
| JP | 4-95023 | 3/1992 |
| JP | 6-172174 | 6/1994 |
| JP | 2004-83523 | 3/2004 |
| JP | 2007-325718 | 12/2007 |
| WO | 2006/041908 | 4/2006 |

OTHER PUBLICATIONS

Machine translation for JP 63-203616 (published Aug. 8, 1988); provided Feb. 17, 2015.*
International Search Report issued Dec. 13, 2011 in International Application No. PCT/JP2011/075354.
Written Opinion of the International Searching Authority issued Dec. 13, 2011 in International Application No. PCT/JP2011/075354.
Rajinder Pal, Viscous Properties of Polymer-Thickened Water-in-Oil-Emulsions, Journal of Applied Polymer Science, 1993, vol. 49, No. 1, p. 65-80.
Office Action issued Jun. 10, 2014 in corresponding Chinese patent application No. 201180063889.2 (with English translation).
Wenjuan Yin, "Research and development of patch", vol. 8, No. 9, pp. 93-94, May 31, 2010 (with English translation).

* cited by examiner

*Primary Examiner* — Jeffrey T Palenik
(74) *Attorney, Agent, or Firm* — Wenderoth, Lind & Ponack, L.L.P.

(57) ABSTRACT

Disclosed is a patch which is a formulation including deposited clonidine crystals and provides stable transdermal absorbability even after storage at varying temperatures. The patch disclosed includes a backing and a medicated layer integrally superposed on one surface of the backing. The medicated layer contains: 5 to 30% by weight of clonidine including clonidine in a crystallized state; 25 to 90% by weight of a macromolecular base (A) having a viscosity-average molecular weight of 800,000 or larger; and 5 to 60% by weight of a liquid additive capable of dissolving the clonidine. The weight ratio of the liquid additive to the macromolecular base (A) [the liquid additive/the macromolecular base (A)] is 0.1 to 2.0.

9 Claims, 4 Drawing Sheets

PATCH

FIELD

The present invention relates to a patch which is a formulation including deposited clonidine crystals and provides stable transdermal absorbability even after storage at varying temperatures.

BACKGROUND

Clonidine is a central antihypertensive drug that stimulates α2 receptors. Patches using clonidine are commercially available in the form of a formulation including deposited crystals. Such clonidine patches can maintain their effect for a long period of time, about one week, after application to the skin. However, the clonidine patches have a problem in that transdermal absorbability changes due to temperature changes during storage. At present, there are no effective measures for the above problem. Therefore, in clinical sites, clonidine patches are required to be stored under strict temperature control such that the temperature does not exceed, for example, 30° C. Accordingly, the storage of clonidine patches imposes a heavy burden on clinical sites.

Patent Literature 1 discloses a clonidine patch comprising a medicated layer containing polyisobutylene (PIB), mineral oil (MO: liquid paraffin), colloidal silica, and clonidine, wherein the ratio of MO to PIB is 1.0 or higher, and the viscosity of the medicated layer is $1.5 \times 10^7$ or higher. The use of such a medicated layer allows the desired transdermal permeability (transdermal absorbability) and viscosity (cohesion) to be ensured. However, there is no description that the transdermal absorbability of the clonidine patch changes due to temperature changes during storage.

Patent Literature 2 discloses a clonidine patch comprising an adhesive layer which is formed on a backing and contains: a copolymer including, as essential components, an alkyl (meth)acrylate having an alkyl group with an average carbon number of 4 or more and a vinyl ester having a polarity parameter of 0 or less; dissolved clonidine; and a dispersed organic acid salt of clonidine. The use of such an adhesive layer prevents the reaction of clonidine with the adhesive and also prevents crystals of clonidine from depositing. However, the technique disclosed in Patent Literature 2 cannot be used for a clonidine patch formulated using only clonidine free base.

CITATION LIST

Patent Literature

Patent Literature 1: Japanese Patent Application Laid-Open No. Sho. 59-206307

Patent Literature 2: Japanese Patent Application Laid-Open No. Hei. 6-172174

SUMMARY

Technical Problem

It is an object of the present invention to provide a patch which is a formulation including deposited clonidine crystals and provides stable transdermal absorbability even after storage at varying temperatures.

Solution to Problem

One possible reason that the transdermal absorbability from the formulation including deposited clonidine crystals changes due to temperature changes during storage is the involvement of change in the crystallized state of clonidine due to temperature change. The base of the clonidine patch is required to have the function of holding clonidine stably and also the function of allowing clonidine present in a crystallized state to be continuously dissolved into the medicated layer and diffused into the skin surface at a desired rate after the patch is applied to the skin. In addition, to prevent the change in the crystallized state due to temperature change, which is the object of the present invention, the temperature dependence of the dissolution and diffusion behavior of clonidine is required to be small. The present inventors have found that to achieve these requirements simultaneously, it is effective to use a base containing prescribed amounts of a macromolecular base having a viscosity-average molecular weight of 800,000 or larger and a liquid additive capable of dissolving clonidine, with the weight ratio of the liquid additive to the macromolecular base having a viscosity-average molecular weight of 800,000 or larger being controlled within a specific range.

The patch of the present invention comprises a backing and a medicated layer integrally superposed on one surface of the backing, the medicated layer containing: 5 to 30% by weight of clonidine including clonidine in a crystallized state; 25 to 90% by weight of a macromolecular base (A) having a viscosity-average molecular weight of 800,000 or larger; and 5 to 60% by weight of a liquid additive capable of dissolving the clonidine, and a weight ratio of the liquid additive to the macromolecular base (A) [the liquid additive/the macromolecular base (A)] being 0.1 to 2.0.

(Clonidine)

The medicated layer of the patch contains clonidine in the form of the free base (2,6-dichloro-N-2-imidazolidinylidenebenzenamine) as an active component (basis). The clonidine in the form of the free base does not include an inorganic acid salt of clonidine such as clonidine hydrochloride or an organic acid salt of clonidine such as clonidine fumarate.

The amount of clonidine in the medicated layer is limited to 5 to 30% by weight and is preferably 5 to 25% by weight, more preferably 8 to 20% by weight, and more preferably 10 to 15% by weight.

If the amount of clonidine in the medicated layer is small, the transdermal absorption rate of clonidine may not be maintained for the desired time, and the amount of transdermal absorption of clonidine may become insufficient, so that the blood level of clonidine cannot be increased to the desired range unless the application area of the patch to the skin is increased. If the amount of clonidine in the medicated layer is large, an excessive amount of crystals of clonidine may be deposited in the medicated layer, so that the cohesion and adhesion of the medicated layer may become insufficient. In such a case, the medicated layer may protrude from the sides of the patch during storage and after application or may be easily peeled off from the backing or the skin. If the amount of clonidine in the medicated layer is excessively large, clonidine is wasted, and it is uneconomical.

The medicated layer contains clonidine in an amount exceeding the upper limit of the amount of clonidine that can be dissolved in the mixture of the macromolecular base and the liquid additive at room temperature. Therefore, part of the clonidine contained in the medicated layer is deposited in a crystallized state, and the rest is dissolved in the macromolecular base and the liquid additive. When the patch is applied to the skin, the dissolved clonidine is first absorbed by the skin by diffusion. With decreased the amount of the dissolved clonidine, the clonidine in the crystallized state is gradually dissolved into the macromolecular base and the liquid additive. To form the medicated layer in which part of clonidine is present in a crystallized state as described above, the following method is used. A medicated layer-forming solution described later is produced such that the produced medicated layer-forming solution contains clonidine in an amount exceeding the upper limit of the amount of clonidine that can be dissolved in the mixture of the macromolecular base and the liquid additive at room temperature, and the medicated layer-forming solution is applied to an appropriate base such as a backing or release liner and then dried. With the above method, a medicated layer in which part of clonidine is deposited in a crystallized state can be formed.

In the present invention, whether or not there is clonidine in a crystallized state in the medicated layer can be determined by the following procedure. First, only the medicated layer is removed from the patch, and the removed medicated layer is cut into a square shape with the side of 2 cm to obtain an observation specimen. Next, the observation specimen is observed under a polarizing microscope at a magnification of 100×, and a photograph is taken. Then the obtained photograph is observed to determine the presence or absence of clonidine in a crystallized state. When crystals having a crystal diameter of 1 μm or larger are observed in the medicated layer, it is determined that clonidine in a crystallized state is present. The crystal diameter means the diameter of the minimum perfect circle that can surround a crystal on the photograph.

(Macromolecular base)

A macromolecular base (A) having a viscosity-average molecular weight of 800,000 or larger is used as the macromolecular base contained in the medicated layer of the patch of the present invention. The present inventors have confirmed that the storage stability of clonidine is improved when the medicated layer contains the macromolecular base (A) having a viscosity-average molecular weight of 800,000 or larger at a prescribed ratio. The detailed mechanism of such an effect is not clear. However, one possible mechanism is as follows. The crystallized state of clonidine contained in the medicated layer can be stabilized. Such stabilization of the crystallized state can highly suppress dissolution and deposition of clonidine present in the crystallized state in the medicated layer due to temperature changes during storage.

The amount of the macromolecular base (A) in the medicated layer is limited to 25 to 90% by weight and is preferably 25 to 85% by weight, more preferably 25 to 50% by weight, and particularly preferably 25 to 45% by weight.

If the amount of the macromolecular base (A) in the medicated layer is small, the cohesion of the medicated layer becomes low. Therefore, the medicated layer is likely to protrude during storage, and the applied medicated layer is not likely to remove without residue. In addition, the above-described dissolution and deposition of the clonidine in the crystallized state occurs easily, so that the transdermal absorbability is likely to change. If the amount of the macromolecular base (A) in the medicated layer is large, the adhesion of the medicated layer may become low, and the diffusion rates of the drug and additive may become low, so that the desired blood level of clonidine may not be obtained.

The viscosity-average molecular weight of the macromolecular base (A) is limited to 800,000 or larger and is preferably 900,000 to 4,000,000, more preferably 1,000,000 to 3,000,000, and particularly preferably 1,000,000 to 1,500,000. As described above, the use of the macromolecular base (A) having a viscosity-average molecular weight of 800,000 or larger can stabilize the crystallized state of clonidine in the medicated layer.

Preferably, the medicated layer further contains a macromolecular base (B) having a viscosity-average molecular weight of 10,000 or larger and less than 800,000, in addition to the macromolecular base (A) having a viscosity-average molecular weight of 800,000 or larger. The use of the macromolecular base (B) allows both high adhesion of the medicated layer and high transdermal absorbability of clonidine to be ensured.

The amount of the macromolecular base (B) in the medicated layer is preferably 1 to 69% by weight, more preferably 1 to 20% by weight, and particularly preferably 1 to 15% by weight.

The viscosity-average molecular weight of the macromolecular base (B) is limited to 10,000 or larger and less than 800,000 and is preferably 10,000 to 400,000, more preferably 20,000 to 100,000, and particularly preferably 20,000 to 50,000. If the viscosity-average molecular weight of the macromolecular base (B) is too small, the cohesion of the medicated layer becomes insufficient, so that the medicated layer is not likely to remove without residue when the patch is peeled off. If the viscosity-average molecular weight of the macromolecular base (B) is too large, the medicated layer becomes hard and is easily peeled off, and the transdermal absorbability of clonidine may become insufficient.

In the present invention, the viscosity-average molecular weights of the macromolecular bases (A) and (B) can be measured as follows. The intrinsic viscosity [η] of a dilute solution of a polymer is determined using, for example, a capillary viscometer, and the viscosity-average molecular weight is computed using the Staudinger's viscosity equation etc.

The macromolecular bases (A) and (B) used are preferably pressure-sensitive adhesives such as rubber-based adhesives, acrylic-based adhesives, and silicon-based adhesives. However, a macromolecular base with no pressure-sensitive adhesion may also be used. Pressure-sensitive adhesives are preferably used because changes in their reactivity and physical properties due to temperature change are small.

Examples of the rubber-based adhesives may include polyisobutylene, polybutadiene, styrene-isoprene-styrene block copolymers, styrene-isoprene-butadiene-styrene block copolymers, and natural rubber.

Commercially available rubber-based adhesives can be used in the present invention. Examples of the commercially available rubber-based adhesive having a viscosity-average molecular weight of 800,000 or larger may include an adhesive available under product name "Vistanex MML-80" (viscosity-average molecular weight: 990,000, manufactured by Exxon Chemical Company), an adhesive available under product name "Oppanol B100" (viscosity-average molecular weight: 1,100,000, manufactured by BASF), an adhesive available under product name "Oppanol B120" (viscosity-average molecular weight: 1,500,000, manufactured by BASF), and an adhesive available under product name "Vistanex MML-140" (viscosity-average molecular weight: 2,100,000, manufactured by Exxon Chemical Company). Examples of the commercially available rubber-based adhesive having a viscosity-average molecular weight of 10,000 or larger and less than 800,000 may include an adhesive available under product name "Oppanol B10SFN" (viscosity-average molecular weight: 36,000, manufactured by BASF) and an adhesive available under product name "Himol 6H" (viscosity-average molecular weight: 60,000, manufactured by Nippon Petrochemicals Co., Ltd.).

Preferred examples of the acrylic-based adhesives may include copolymers containing 60% by weight or more of an alkyl (meth)acrylate component having an alkyl group with 1 to 20 carbon atoms. The type of alkyl (meth)acrylate having an alkyl group with 1 to 20 carbon atoms is not particularly limited, and examples thereof may include methyl acrylate, methyl methacrylate, hexyl acrylate, hexyl methacrylate, octyl acrylate, octyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, octadecyl acrylate, and octadecyl methacrylate. In the present invention, (meth)acrylate means acrylate or methacrylate.

The above copolymer may further include an additional monomer component other than the alkyl (meth)acrylate having an alkyl group with 1 to 20 carbon atoms. Examples of the additional monomer may include: polyfunctional monomers having two or more polymerizable functional groups in their molecule such as divinylbenzene, methylene bisacrylic amide, ethylene glycol dimethacrylate, and ethylene glycol diacrylate; acrylic acid; methacrylic acid; vinylpyrrolidone; vinyl acetate; and hydroxyalkyl (meth)acrylates. By adding such a monomer, the dissolvability and diffusibility of clonidine in the medicated layer and the adhesion of the patch can be controlled. In the present invention, (meth)acrylic acid means acrylic acid or methacrylic acid.

Of the above monomers, alkyl (meth)acrylate copolymers having no polar functional group are preferred from the viewpoint of the adhesion properties and the ability to dissolve clonidine. A copolymer containing 60% by weight or more of an alkyl methacrylate component having an alkyl group with 6 to 20 carbon atoms is more preferred, and a copolymer containing 70% by weight or more of an alkyl methacrylate component having an alkyl group with 6 to 20 carbon atoms is particularly preferred. Examples of the polar functional group may include a hydroxyl group, an amino group, and a carboxyl group. Other examples of the commercially available acrylic-based adhesive may include DURO-TAK (registered trademark) 87-4098.

Other macromolecular bases such as vinyl-based macromolecular materials, e.g., polyvinyl alkyl ethers, polyvinyl acetate, a partially saponified product of polyvinyl acetate, polyvinyl alcohol, and polyvinylpyrrolidone, may also be used. These macromolecular materials are effective for controlling adhesion. However, their ability to dissolve clonidine is relatively high, so that if the amount of these macromolecular materials is too large, clonidine in a crystallized state cannot be held. Therefore, when such macromolecular material is added to the medicated layer, the amount of the macromolecular material in the medicated layer is preferably 1 to 20% by weight and more preferably 1 to 10% by weight.

Particularly, the macromolecular base (A) is preferably a rubber-based adhesive or an alkyl (meth)acrylate copolymer having no polar functional group and more preferably polyisobutylene, because these bases (A) sufficiently provide the effects of the present invention, also provide good stability of the drug, and have less skin irritation.

Similarly, the macromolecular base (B) is preferably a rubber-based adhesive or an alkyl (meth)acrylate copolymer having no polar functional group and more preferably polyisobutylene, because the base (B) provides the effects of the present invention sufficiently, also provides good stability of the drug, and has less skin irritation.

(Liquid Additive)

The patch of the present invention is used with its medicated layer applied to the skin, and clonidine contained in the medicated layer is absorbed through the skin. The patch is required to be capable of maintaining the stable transdermal absorption rate of clonidine. To maintain the stable transdermal absorption rate of clonidine, it is required to keep the solubility and diffusivity of clonidine in the surface of the medicated layer constant. In the present invention, it has been found that the transdermal absorption rate of clonidine can be maintained constant by adding, to the medicated layer, a predetermined amount or more of a liquid additive that can dissolve clonidine and controlling the weight ratio of the liquid additive to the macromolecular base (A) having a viscosity-average molecular weight of 800,000 or larger in the medicated layer within a prescribed range. It has also been found that the above controlled addition of the liquid additive can provide good storage stability and adhesion of the medicated layer.

As described above, part of clonidine contained in the medicated layer is deposited and present in a crystallized state, and the rest is dissolved in the macromolecular bases and the liquid additive. When the patch is applied to the skin, the clonidine dissolved in the medicated layer is first absorbed into the skin by diffusion, and then the clonidine in the crystallized state is gradually dissolved in the medicated layer. In this case, the dissolution rate and diffusion rate of clonidine are influenced by the ratio of the liquid additive to the macromolecular base (A). The higher the ratio of the liquid additive to the macromolecular base (A) becomes, the higher the dissolution rate and diffusion rate of clonidine becomes, and the further the transdermal absorbability is improved. However, as the ratio of the liquid additive increases, the change in the solubility of clonidine due to temperature change during storage increases. This causes a phenomenon that the clonidine dissolved at high temperature migrates to the medicated layer surface or the interface between the medicated layer and the backing, and is then deposited there at low temperate. Therefore, the transdermal absorbability of clonidine may decrease or increase during storage. These changes in the properties of clonidine tend to occur significantly when the amount of clonidine contained in the medicated layer is 5% by weight or larger.

The weight ratio of the liquid additive to the macromolecular base (A) in the medicated layer [the liquid additive/the macromolecular base (A)] is limited within the range of 0.1 to 2.0 and is preferably 0.5 to 1.9 and more preferably 0.7 to 1.7. If the weight ratio of [the liquid additive/the macromolecular base (A)] is less than 0.1, the transdermal absorbability of clonidine may become insufficient. If the weight ratio of [the liquid additive/the macromolecular base (A)] exceeds 2.0, the cohesion of the medicated layer may become insufficient, and the change in transdermal absorbability of clonidine may easily occur.

The amount of the liquid additive in the medicated layer is limited to 5 to 60% by weight and is preferably 10 to 50% by weight and more preferably 25 to 50% by weight. If the amount of the liquid additive is less than 5% by weight, the transdermal absorbability of clonidine and its duration may become insufficient. If the amount of the liquid additive exceeds 60%, the cohesion of the medicated layer becomes insufficient, and the medicated layer is likely to protrude during storage and after application. If the amount of the liquid additive exceeds 60%, the change in the ability to dissolve clonidine due to temperature change becomes significant, so that the crystallized state of clonidine during storage is likely to change. Therefore, the properties of the medicated layer, such as transdermal absorbability and adhesion, may change.

The medicated layer comprises the liquid additive which can dissolve clonidine. More specifically, it is preferable that the liquid additive can dissolve 0.001 to 30 parts by weight of clonidine in 100 parts by weight of the liquid additive at 25° C.

Examples of the liquid additive that can dissolve clonidine may include: hydrocarbons such as liquid paraffin and squalane; esters of fatty acids and monohydric or polyhydric alcohols such as isopropyl myristate, isopropyl palmitate, glycerin monolaurate, diethyl sebacate, and medium-chain fatty acid triglyceride; higher fatty acids such as oleic acid and isostearic acid; higher alcohols such as isostearyl alcohol, octyldodecanol, and hexyldecanol; polyhydric alcohols such as polyethylene glycol, polyoxyethylene, and polyoxypropylene glycol; and natural fats and natural oils such as olive oil and coconut oil.

(Other Components)

The medicated layer may contain additives such as a filler, a stabilizer, and a adhesion adjuster, so long as the performance of the medicated layer is not impaired. For example, the filler is added in order to control the adhesion of the medicated layer and to control the releasability of the drug. Examples of the filler may include calcium carbonate, titanium oxide, lactose, crystalline cellulose, silicic acid anhydride, bentonite, and talc. Of these, silicic acid anhydride is preferred, and light silicic acid anhydride is more preferred, because the stability of clonidine and the adhesion of the medicated layer can be ensured by using them.

If the amount of the filler in the medicated layer is small, the effect due to the addition of the filler to the medicated layer may not be exerted. If the amount of the filler in the medicated layer is large, the adhesion may become low, or the transdermal absorbability and stability of the drug may be adversely affected. Therefore, the amount of the filler in the medicated layer is preferably 1 to 20% by weight and more preferably 2 to 10% by weight.

The stabilizer is added for the purpose of suppressing the decomposition of the drug in the medicated layer, changes in the physical properties of the macromolecular bases, and discoloration. Examples of the stabilizer may include: antioxidants such as butylhydroxytoluene, sorbic acid, and tocopherol acetate; cyclodextrin; and ethylenediaminetetraacetic acid. The amount of the stabilizer in the medicated layer may be 0.05 to 10% by weight.

The thickness of the medicated layer is appropriately set within the range in which the amount of clonidine that allows its absorbability to be maintained can be ensured and good adhesion can be achieved. The thickness is preferably 20 to 200 μm and more preferably 30 to 120 μm. If the thickness of the medicated layer is smaller than 20 μm, a sufficient amount of clonidine cannot be held, and also sufficient adhesion when the patch is applied to the skin may not be exerted. If the thickness of the medicated layer exceeds 200 μm, the medicated layer contains more clonidine than necessary. Therefore, clonidine is wasted, and the medicated layer is likely to protrude from the sides of the patch during storage. In such a case, the patch may be difficult to be removed from the package upon use.

In the patch of the present invention, the medicated layer is integrally superposed on one surface of the backing. Only one medicated layer may be integrally superposed on the one surface of the backing, or two or more medicated layers may be integrally superposed on the one surface of the backing.

Examples of the patch including two medicated layers integrally superposed on one surface of the backing may include a patch comprising a backing, a first medicated layer integrally superposed on one surface of the backing, and a second medicated layer integrally superposed on one surface of the first medicated layer. In the patch including a plurality of medicated layers superposed on each other, the rate and amount of clonidine transferring from the medicated layers to the skin can be easily controlled within the desired ranges.

Preferably, the first medicated layer contains: 10 to 30% by weight of clonidine including clonidine in a crystallized state; 25 to 50% by weight of the macromolecular base (A) having a viscosity-average molecular weight of 800,000 or larger; and 30 to 55% by weight of the liquid additive that can dissolve the clonidine. In addition, the weight ratio of the liquid additive to the macromolecular base (A) [the liquid additive/the macromolecular base (A)] is preferably 0.5 to 2.0.

Preferably, the second medicated layer contains: 5% by weight or larger and less than 10% by weight of clonidine including clonidine in a crystallized state; 25 to 50% by weight of the macromolecular base (A) having a viscosity-average molecular weight of 800,000 or larger; and 30 to 55% by weight of the liquid additive that can dissolve the clonidine. In addition, the weight ratio of the liquid additive to the macromolecular base (A) [the liquid additive/the macromolecular base (A)] is preferably 0.5 to 2.0.

Each of the first and second medicated layers may contain additional additives such as a filler, a stabilizer, and a adhesion adjuster. The details of the clonidine, macromolecular base (A), macromolecular base (B), liquid additive, and additional additives, used for the first and second medicated layers, are as described above.

(Adhesive Layer)

Preferably, an adhesive layer containing clonidine in an amount (% by weight) smaller than that in the medicated layer is integrally superposed on one surface of the medicated layer. The adhesive layer is generally integrally superposed on the surface of the medicated layer that faces the skin. By providing the adhesive layer, the adhesion to the skin can be further improved while the transdermal absorbability of clonidine and its duration are maintained.

The composition of the adhesive layer is not particularly limited, so long as the transdermal absorption from the medicated layer is not prevented and the purpose of improving the adhesion of the formulation can be achieved. For example, the adhesive layer may contain the same components as those of the medicated layer but has a composition in which the concentration of clonidine is reduced within the range in which more preferred adhesion is obtained.

Preferably, the adhesive layer contains clonidine, a macromolecular base (A) having a viscosity-average molecular weight of 800,000 or larger, and a liquid additive that can dissolve clonidine. More preferably, the adhesive layer further contains a macromolecular base (B) having a viscosity-average molecular weight of 10,000 or larger and less than 800,000, in addition to the above components. The clonidine, the macromolecular base (A), the liquid additive, and the macromolecular base (B), used for the adhesive layer, may be the same as those for the above-described medicated layer.

The amount of clonidine in the adhesive layer is preferably 0.5 to 3% by weight and more preferably 0.7 to 2% by weight. If the amount of clonidine in the adhesive layer is small, the transdermal absorption rate of clonidine may not be maintained for the desired time, or the amount of transdermal absorption of clonidine may become insufficient. In such a case, the blood level of clonidine cannot be increased to the desired range unless the application area of the patch to the skin is increased. If the amount of clonidine in the adhesive layer is large, the adhesion of the adhesive layer may become low.

The amount of the macromolecular base (A) in the adhesive layer is preferably 25 to 90% by weight, more preferably 25 to 60% by weight, and particularly preferably 25 to 45% by weight. If the amount of the macromolecular base (A) in the adhesive layer is small, the cohesion of the adhesive layer becomes low. Therefore, the adhesive layer is likely to protrude during storage, and the applied adhesive layer is not likely to remove without residue. If the amount of the macromolecular base (A) in the adhesive layer is large, the adhesion of the adhesive layer may become low, and the diffusion rates of the drug and additives may become low, so that the desired blood level of clonidine may not be obtained.

When the adhesive layer contains the macromolecular base (B), the amount of the macromolecular base (B) in the adhesive layer is preferably 1 to 25% by weight, more preferably 1 to 20% by weight, and particularly preferably 1 to 15% by weight. If the amount of the macromolecular base (B) in the adhesive layer is small, the adhesion of the adhesive layer may become low. If the amount of the macromolecular base (B) in the adhesive layer is large, the cohesion of the adhesive layer becomes low. Therefore, the adhesive layer is likely to protrude during storage, and the applied adhesive layer is not likely to remove without residue.

The amount of the liquid additive in the adhesive layer is preferably 5 to 60% by weight, more preferably 10 to 50% by weight, and particularly preferably 30 to 50% by weight. If the amount of the liquid additive in the adhesive layer is small, the transdermal absorbability of clonidine and its duration may become insufficient. If the amount of the liquid additive in the adhesive layer is large, the cohesion of the adhesive layer becomes low. Therefore, the adhesive layer is likely to protrude during storage, and the applied adhesive layer is not likely to remove without residue.

The weight ratio of the liquid additive to the macromolecular base (A) in the adhesive layer [the liquid additive/the macromolecular base (A)] is preferably 0.1 to 2.0, more preferably 0.5 to 1.9, and particularly preferably 0.7 to 1.7. If the weight ratio [the liquid additive/the macromolecular base (A)] in the adhesive layer is less than 0.1, the transdermal absorbability of clonidine and its duration may become insufficient. If the weight ratio [the liquid additive/the macromolecular base (A)] in the adhesive layer exceeds 2.0, the cohesion of the adhesive layer becomes low. Therefore, the adhesive layer is likely to protrude during storage, and the applied adhesive layer is not likely to remove without residue.

The thickness of the adhesive layer is preferably 20 to 200 µm and more preferably 25 to 200 µm. If the thickness of the adhesive layer is less than 20 µm, the adhesion of the adhesive layer may become insufficient. If the thickness of the adhesive layer exceeds 200 µm, the adhesive layer is likely to protrude from the sides of the patch during storage.

The adhesive layer may contain additional additives such as a filler, a stabilizer, and a adhesion adjuster. The additional additives used for the adhesive layer may be the same as those for the medicated layer.

(Control Layer)

When the patch of the present invention includes the above-described first and second medicated layers, the patch preferably comprises a control layer between the first and second medicated layers. The first medicated layer, the control layer, and the second medicated layer are integrally superposed in this order for use on one surface of the backing. The use of the control layer further improves the duration of clonidine absorption.

Also when the patch of the present invention includes the above-described adhesive layer, the patch preferably comprises a control layer between the medicated layer and the adhesive layer. The control layer and the adhesive layer are integrally superposed in this order on one surface of the medicated layer. The use of the control layer can further improve the duration of clonidine absorption.

The control layer preferably comprises a polymer that has no influence on the stability of clonidine and can provide close adhesion between the medicated layer and the adhesive layer or close adhesion between the first and second medicated layers. Specific examples of the polymer may include polyethylene terephthalate, nylon, cellulose acetate, ethyl cellulose, rayon, vinyl acetate-vinyl chloride copolymers, plasticized polyvinyl chloride, polyurethane, polyolefin-based resins, ethylene-vinyl acetate copolymers, ethylene-methyl (meth)acrylate copolymers, polyvinylidene chloride, and polyvinyl alcohol. These polymers can be used as a film having no pores or a porous film having uniformly distributed pores.

The thickness of the control layer and the size and number of the pores are appropriately controlled according to the expected control level of the diffusion rate of clonidine.

Preferably, the control layer used is a porous film formed of any of the above polymers and having a large number of through holes extending between opposite sides of the porous film, and the porous film has been impregnated with a liquid additive. The use of the control layer including the porous polymer film impregnated with the liquid additive allows the diffusion rate of clonidine to be controlled, so that a change in the crystallized state of clonidine due to temperature change can be further suppressed. The liquid additive used may be the same as that for the medicated layer.

The porous film is formed of preferably a polyolefin-based resin and more preferably polyethylene or polypropylene. The use of the porous polyolefin-based resin film formed of polyolefin-based resin can improve the duration of clonidine absorption.

The porous film can be impregnated with the liquid additive by filling the through holes included in the porous film with the liquid additive.

(Backing)

The type of backing to be used is not limited, so long as it is flexible but can play a role in providing self-supportability to the patch and preventing loss of the drug. Examples of the material forming such a backing may include polyethylene terephthalate, nylon, cellulose acetate, ethyl cellulose, rayon, plasticized vinyl acetate-vinyl chloride copolymers, plasticized polyvinyl chloride, polyurethane, polyethylene, ethylene-vinyl acetate copolymers, ethylene-methyl (meth)acrylate copolymers, polyvinylidene chloride, aluminum, polyvinyl alcohol, and cotton. Of these, polyethylene terephthalate is preferred.

The form of the backing is not particularly limited, and examples thereof may include a film, a foamed body, and fabrics such as a nonwoven fabric, a woven fabric, and a knitted fabric. The backing may be composed of a superposed and integrated body of a plurality of backings. For example, from the viewpoint of flexibility and prevention of loss of the drug, it is possible to use a laminated film produced by integrally superposing a nonwoven fabric or a flexible resin film of, for example, an ethylene-vinyl acetate copolymer on a polyethylene terephthalate film as the backing. In addition, by providing a vapor-deposition layer or a metal foil layer of, for example, aluminum on at least one side of the backing, the light shielding properties and barrier properties of the backing can be improved. The method of superposing and integrating a plurality of backings on each other is not particularly limited, and examples of the method may include a method using an adhesive or a method using heat fusion.

Particularly, a polyethylene terephthalate film is preferably used as the backing because the damage to the patch can be effectively prevented.

The thickness of the backing is preferably 10 to 200 μm and more preferably 15 to 100 μm.

To tightly integrate the medicated layer into the backing, the surface of the backing on which the medicated layer is integrally superposed may have some irregularities, may be subjected to corona treatment or plasma discharge treatment, or coated with an anchor coating agent.

(Release Liner)

Preferably, for the purpose of preventing loss of clonidine in the medicated layer and the adhesive layer and of protecting the medicated layer and the adhesive layer, release liner is releasably stacked on the surface of the medicated layer or on the surface of the adhesive layer when the patch has the adhesive layer. Examples of the release liner may include paper and resin films formed of polyethylene terephthalate, polyethylene, polypropylene, polyvinyl chloride, and polyvinylidene chloride. Preferably, the release liner has been subjected to release treatment on the surface facing the medicated layer. The release liner may include a single layer or a plurality of layers. For the purpose of improving the barrier properties of the release liner, an aluminum foil or an aluminum vapor-deposition layer may be provided on the release liner. When the release liner is formed of paper, the release liner may be impregnated with a resin such as polyvinyl alcohol, for the purpose of improving the barrier properties of the release liner.

(Production Method)

A method of producing the patch of the present invention will next be described. The method of producing the patch is not particularly limited. For example, first, components for forming the medicated layer and other optional solvents are added and mixed uniformly to prepare a medicated layer-forming solution. Then, the medicated layer-forming solution is spread on the backing using a well-known coating process such as a solvent coating process, a hot-melt process, or a calender process to thereby obtain the medicated layer.

For example, the solvent coating process may be carried out as follows. First, clonidine, the macromolecular base (A), the liquid additive, and optionally other additives, and a solvent such as toluene are mixed and stirred until uniform to prepare a medicated layer-forming solution. Then the medicated layer-forming solution is applied to one surface of the backing using a coater and dried to obtain a medicated layer integrally superposed on the one surface of the backing. Preferably, release liner subjected to release treatment with, for example, silicon is then stacked on the surface of the medicated layer such that the surface of the release liner that has been subjected to release treatment faces the medicated layer. The following method can also be used. After the medicated layer-forming solution is prepared in the manner described above, the medicated layer-forming solution is applied to the release-treated surface of release liner by the same coating process as described above and dried to form a medicated layer on the release liner. Then the backing is integrally superposed on the medicated layer.

Examples to form an adhesive layer on one surface of the medicated layer include the following method. First, clonidine, the macromolecular base (A), the liquid additive, and optionally added additives, and a solvent such as toluene are mixed and stirred until uniform to prepare an adhesive layer-forming solution. Then the adhesive layer-forming solution is applied to the release-treated surface of release liner by the same coating process as described above and dried to form an adhesive layer on the release liner. Then the adhesive layer is integrally superposed on the medicated layer.

Advantageous Effects of Invention

In the patch of the present invention, the weight ratio of the liquid additive to the macromolecular base (A) falls within the specific range, so that clonidine dissolved in the medicated layer can be prevented from being concentrated on the surface of the medicated layer. Therefore, even when a temperature change occurs during storage, excessive deposition of clonidine on the surface of the medicated layer is suppressed, and the state in which part of clonidine contained in the medicated layer is deposited uniformly over the entire medicated layer as fine crystals can be maintained, so that the storage stability of the patch can be improved. In the patch of the present invention, since part of clonidine is deposited uniformly over the entire medicated layer as fine crystals, a constant amount of clonidine can be continuously absorbed into the skin. In addition, in the patch of the present invention, the cohesion of the medicated layer is high, and adhesion and shape-retaining properties during storage are also high.

The patch of the present invention has the above-described configuration. Therefore, even when a temperature change occurs during storage of the formulation including deposited clonidine crystals, the change in transdermal absorbability is suppressed, and temperature (quality) control during distribution and storage can be facilitated.

DESCRIPTION OF EMBODIMENTS

The present invention will next be described more specifically by way of Examples, but the invention is not limited thereto.

EXAMPLES

Example 1

Thirty nine Parts by weight of a liquid additive (liquid paraffin, product name: HICALL M72, manufactured by KANEDA Co., Ltd.), 13 parts by weight of clonidine, 8 parts by weight of light silicic acid anhydride (product name: AEROSIL 200, manufactured by Nippon Aerosil Co., Ltd.), and 560 parts by weight of toluene were stirred until uniform to obtain a mixed solution. Then 28 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 12 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was mixed uniformly to prepare a medicated layer-forming solution. The obtained medicated layer-forming solution was applied to 38 μm-thick release liner made of polyethylene terephthalate (PET) and having a silicon-treated surface to a dry thickness of 50 and dried in an oven at 80° C. for 60 minutes to obtain a medicated layer (thickness: 50 μm). Then a 25 μm-thick PET film was prepared as a backing. The PET film was superposed on the surface of the medicated layer and pressed thereagainst to integrally superpose the backing on the surface of the medicated layer, and a patch in Example 1 was thereby obtained.

Example 2

Thirty eight Parts by weight of a liquid additive (liquid paraffin, product name: HICALL M72, manufactured by KANEDA Co., Ltd.), 3 parts by weight of clonidine, 9 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 35 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 15 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was mixed uniformly to prepare an adhesive layer-forming solution. The obtained adhesive layer-forming solution was applied to PET release liner having a silicon-treated surface to a dry thickness of 50 μm and dried in an oven at 80° C. for 60 minutes to obtain an adhesive layer (thickness: 50 μm). A 25 μm-thick porous polypropylene film (product name: Celgard #2400, manufactured by Celgard, LLC) pre-impregnated with a liquid additive (liquid paraffin, product name: HICALL M72, manufactured by KANEDA Co., Ltd.) in an amount of 9 g/m² was integrally superposed on the surface of the adhesive layer. Then the medicated layer of Example 1 with the PET release liner removed was integrally superposed on the porous polypropylene film to obtain a patch in Example 2. The porous polypropylene film had a large number of through holes extending between the opposite surfaces thereof.

Example 3

Forty seven Parts by weight of a liquid additive (liquid paraffin, product name: HICALL M72, manufactured by KANEDA Co., Ltd.), 13 parts by weight of clonidine, 8 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 29 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 3 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was mixed uniformly to prepare a medicated layer-forming solution. The obtained medicated layer-forming solution was applied to polyethylene terephthalate-made release liner having a silicon-treated surface to a dry thickness of 50 μm and dried in an oven at 80° C. for 60 minutes to obtain a medicated layer (thickness: 50 μm). Then a 25 μm-thick PET film was prepared as a backing. The PET film was superposed on the surface of the medicated layer and pressed thereagainst to integrally superpose the backing on the surface of the medicated layer.

Separately, 47 parts by weight of a liquid additive (liquid paraffin, product name: HICALL M72, manufactured by KANEDA Co., Ltd.), 3 parts by weight of clonidine, 8 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 39 parts by weight of macromolecular base (A) having a viscosity-average molecular weight of 800,000 or larger (high-molecular weight polyisobutylene, viscosity-average molecular weight: 1,100,000, product name: Oppanol B100, manufactured by BASF) and 3 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was stirred uniformly to prepare an adhesive layer-forming solution. The obtained adhesive layer-forming solution was applied to PET release liner having a silicon-treated surface to a dry thickness of 50 μm and dried in an oven at 80° C. for 60 minutes to obtain an adhesive layer (thickness: 50 μm). A 25 μm-thick porous polypropylene film (product name: Celgard #2400, manufactured by Celgard, LLC) pre-impregnated with a liquid additive (liquid paraffin, product name: HICALL. M72, manufactured by KANEDA Co., Ltd.) in an amount of 9 g/m² was integrally superposed on the surface of the adhesive layer. Then the medicated layer of Example 3 with the PET release liner removed was integrally superposed on the porous polypropylene film to obtain a patch in Example 3. The porous polypropylene film had a large number of through holes extending between the opposite surfaces thereof.

Example 4

Thirty nine Parts by weight of a liquid additive (liquid paraffin, product name: HICALL M72, manufactured by KANEDA Co., Ltd.), 1 part by weight of clonidine, 9 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 36 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 15 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was mixed uniformly to prepare an adhesive layer-forming solution. A patch of Example 4 was obtained by repeating the same procedure as in Example 2 except that the above adhesive layer-forming solution was used.

Example 5

Twenty eight Parts by weight of a liquid additive (liquid paraffin, product name: HICALL M72, manufactured by KANEDA Co., Ltd.), 13 parts by weight of clonidine, 8 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 40 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 11 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was uniformly mixed to prepare a medicated layer-forming solution. The obtained medicated layer-forming solution was applied to polyethylene terephthalate-made release liner (thickness: 38 μm) having a silicon-treated surface to a dry thickness of 50 μm and dried in an oven at 80° C. for 90 minutes to obtain a medicated layer (thickness: 50 μm). Then a 25 μm-thick PET film was prepared as a backing. The PET film was superposed on the surface of the medicated layer and pressed thereagainst to integrally superpose the backing on the surface of the medicated layer.

Separately, 39 parts by weight of a liquid additive (liquid paraffin, product name: HICALL M72, manufactured by KANEDA Co., Ltd.), 1 part by weight of clonidine, 9 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 36 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 15 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was stirred uniformly to prepare an adhesive layer-forming solution. The obtained adhesive layer-forming solution was applied to PET release liner having a silicon-treated surface to a dry thickness of 50 μm and dried in an oven at 80° C. for 60 minutes to obtain an adhesive layer (thickness: 50 μm). A 25 μm-thick porous polypropylene film (product name: Celgard #2400, manufactured by Celgard, LLC) pre-impregnated with a liquid additive (liquid paraffin, product name: HICALL M72, manufactured by KANEDA Co., Ltd.) in an amount of 9 g/m² was integrally superposed on the surface of the adhesive layer. Then the medicated layer of Example 5 with the PET release liner removed was integrally superposed on the porous polypropylene film to obtain a patch of Example 5. The porous polypropylene film had a large number of through holes extending between the opposite surfaces thereof.

Examples 6 to 10 and Comparative Example 3

Patches were produced as in Example 5 except that the amounts of clonidine, the macromolecular base (A), the macromolecular base (B), the liquid additive, and light silicic acid anhydride in the medicated layer and the adhesive layer and the thickness of the adhesive layer were changed as described in TABLEs 4 and 5.

Example 11

Forty seven Parts by weight of a liquid additive (liquid paraffin, product name: HICALL M72, manufactured by KANEDA Co., Ltd.), 1 part by weight of clonidine, 8 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 30 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 14 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was uniformly mixed to prepare an adhesive layer-forming solution. The obtained adhesive layer-forming solution was applied to polyethylene terephthalate-made release liner (thickness: 38 μm) having a silicon-treated surface to a dry thickness of 50 μm and dried in an oven at 80° C. for 90 minutes to obtain an adhesive layer (I) (thickness: 50 μm).

Next, an adhesive layer-forming solution was prepared in the same manner as described above. The obtained adhesive layer-forming solution was applied to polyethylene terephthalate-made release liner (thickness: 38 μm) having a silicon-treated surface to a dry thickness of 30 μm and dried in an oven at 80° C. for 90 minutes to obtain an adhesive layer (II) (thickness: 30 μm). By repeating the above procedure, two adhesive layers (II) were produced.

The two adhesive layers (II) with the PET-made release liner removed therefrom were superposed on the surface of the adhesive layer (I) formed on the PET-made release liner to thereby obtain an adhesive layer (thickness: 110 μm). A 25 μm-thick porous polypropylene film (product name: Celgard #2400, manufactured by Celgard, LLC) pre-impregnated with a liquid additive (liquid paraffin, product name: HICALL M72, manufactured by KANEDA Co., Ltd.) in an amount of 9 g/m² was integrally superposed on the surface of the adhesive layer. Then the medicated layer in Example 9 with the PET release liner removed was integrally superposed on the porous polypropylene film to obtain a patch in Example 11. The porous polypropylene film had a large number of through holes extending between the opposite surfaces thereof.

Example 12

Forty seven Parts by weight of a liquid additive (liquid paraffin, product name: HICALL M72, manufactured by KANEDA Co., Ltd.), 1 part by weight of clonidine, 8 parts by weight of light silicic acid anhydride (product name: AERO- SIL 200, manufactured by Nippon Aerosil Co., Ltd.), and 560 parts by weight of toluene were mixed and stirred until uniform to obtain a mixed solution. Then 30 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 14 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was mixed uniformly to prepare an adhesive layer-forming solution. The obtained adhesive layer-forming solution was applied to polyethylene terephthalate-made release liner (thickness: 38 µm) having a silicon-treated surface to a dry thickness of 50 µm and dried in an oven at 80° C. for 90 minutes to obtain an adhesive layer (I) (thickness.: 50 µm). By repeating the above procedure, three adhesive layers (I) were produced.

The PET release liner was removed from two of the three adhesive layers (I), and the two adhesive layers (I) with the PET release liner removed were integrally superposed on the surface of the remaining adhesive layer (I) formed on the PET release liner to thereby obtain an adhesive layer (thickness: 150 µm). A patch of Example 12 was obtained by repeating the same procedure as in Example 11 except that the above-produced adhesive layer was used.

Example 13

Forty seven Parts by weight of a liquid additive (liquid paraffin, product name: HICALL M72, manufactured by KANEDA Co., Ltd.), 1 part by weight of clonidine, 8 parts by weight of light silicic acid anhydride (product name: AEROSIL 200, manufactured by Nippon Aerosil Co., Ltd.), and 560 parts by weight of toluene were mixed and stirred until uniform to obtain a mixed solution. Then 30 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 14 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was uniformly mixed to prepare an adhesive layer-forming solution. The obtained adhesive layer-forming solution was applied to polyethylene terephthalate-made release liner (thickness: 38 µm) having a silicon-treated surface to a dry thickness of 50 µm and dried in an oven at 80° C. for 90 minutes to obtain an adhesive layer (I) (thickness: 50 µm). By repeating the above procedure, four adhesive layers (I) were produced.

The PET release liner was removed from three of the four adhesive layers (I). The three adhesive layers (I) with the PET release liner removed were integrally superposed on the surface of the remaining adhesive layer (I) formed on the PET release liner to thereby obtain an adhesive layer (thickness: 200 µm). A patch of Example 13 was obtained by repeating the same procedure as in Example 11 except that the above-produced adhesive layer was used.

Comparative Example 1

Forty seven Parts by weight of a liquid additive (liquid paraffin, product name: HICALL M72, manufactured by KANEDA Co., Ltd.), 13 parts by weight of clonidine, 8 parts by weight of light silicic acid anhydride (product name: AEROSIL 200, manufactured by Nippon Aerosil Co., Ltd.), and 560 parts of toluene were stirred until uniform to obtain a mixed solution. Then 20 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 12 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was mixed uniformly to prepare a medicated layer-forming solution. A patch of Comparative Example 1 was obtained by repeating the same procedure as in Example 1 except that the above medicated layer-forming solution was used.

Comparative Example 2

Forty seven Parts by weight of a liquid additive (liquid paraffin, product name: HICALL M72, manufactured by KANEDA Co., Ltd.), 3 parts by weight of clonidine, 9 parts by weight of light silicic acid anhydride (product name: AEROSIL 200, manufactured by Nippon Aerosil Co., Ltd.), and 560 parts by weight or toluene were mixed and stirred until uniform to obtain a mixed solution. Then 29 parts by weight of a macromolecular base (A) having a viscosity-average molecular weight of 800,000 or larger (high-molecular weight polyisobutylene, viscosity-average molecular weight: 1,100,000, product name: Oppanol B100, manufactured by BASF) and 12 parts by weight of a macromolecular base (B) having a viscosity-average molecular weight of 10,000 or larger and less than 800,000 (low-molecular weight polyisobutylene, viscosity-average molecular weight: 36,000, product name: Oppanol B10SFN, manufactured by BASF) were added to the mixed solution. The mixture was uniformly mixed to prepare an adhesive layer-forming solution. The obtained adhesive layer-forming solution was applied to 38 µm PET release liner having a silicon-treated surface to a dry thickness of 50 µm and dried in an oven at 80° C. for 60 minutes to obtain an adhesive layer (thickness: 50 µm). A 25 µm-thick porous polypropylene film impregnated with a liquid additive (liquid paraffin, product name: HICALL M72, manufactured by KANEDA Co., Ltd.) in an amount of 9 g/m$^2$ was integrally superposed on the surface of the adhesive layer. Then the medicated layer of Comparative Example 1 with the release liner removed was integrally superposed on the porous polypropylene film to obtain a patch in Comparative Example 2. The porous polypropylene film had a large number of through holes extending between the opposite surfaces thereof.

(Evaluation: Methods and Results)
1. Observation of Crystals under Polarizing Microscope (Immediately After Production)

Each of the medicated layers that had been formed on the release liner in the Examples and Comparative Examples but had not been integrally superposed on the PET films was removed from the release liner immediately after production. Then the medicated layer was cut into a square shape of side 2 cm to obtain an observation sample. Next, the observation sample was observed under a polarizing microscope at a magnification of 100×, and a photograph was taken. The obtained photograph was observed to determine the presence or absence of clonidine in a crystallized state. When crystals having a crystal diameter of 1 μm or larger were observed, it was determined that clonidine in a crystallized state was deposited. The crystal diameter means the diameter of the minimum perfect circle that can surround a crystal on the photograph. Clonidine deposited in a crystallized state was confirmed in all the medicated layers produced in the Examples and Comparative Examples.

2. Observation of Crystals under Polarizing Microscope (Storage at 25° C., 40° C., and 60° C.)

Figure 1:
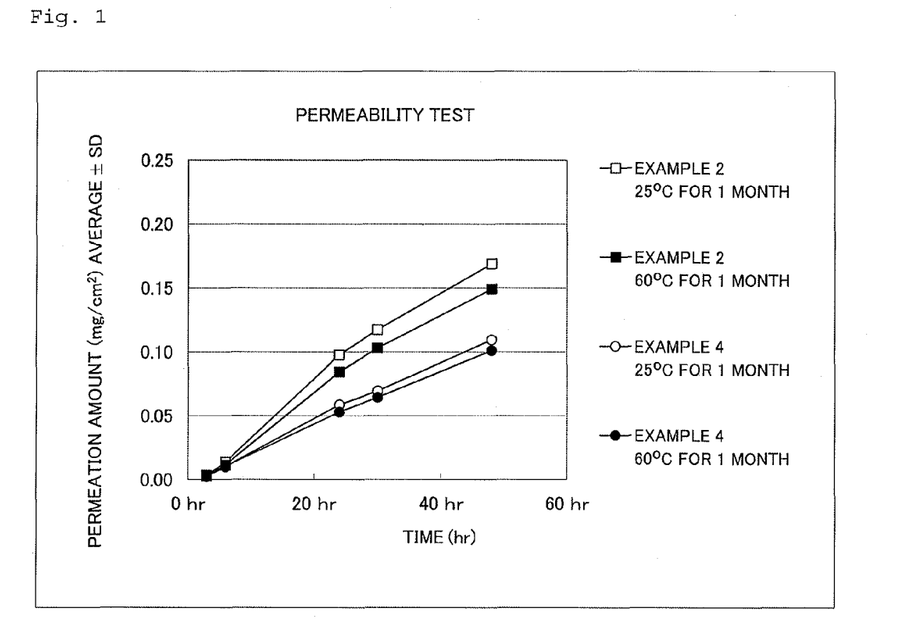
FIG. 1 is a graph showing the results of a permeability test performed on patches of Examples 2 and 4 stored at 25° C. or 60° C. for one month.
Figure 2:
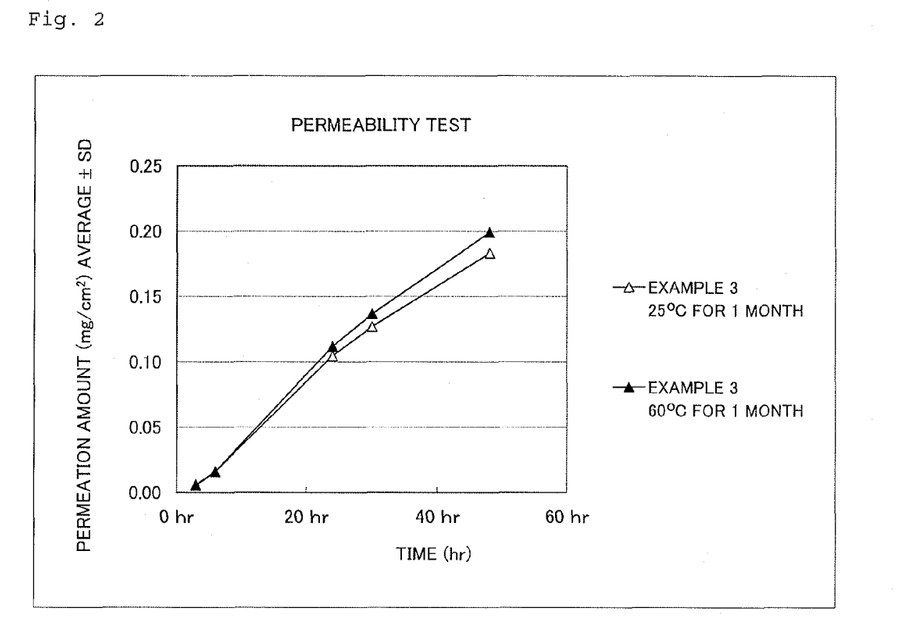
FIG. 2 is a graph showing the results of a permeability test performed on patches of Example 3 stored at 25° C. or 60° C. for one month.
Figure 3:
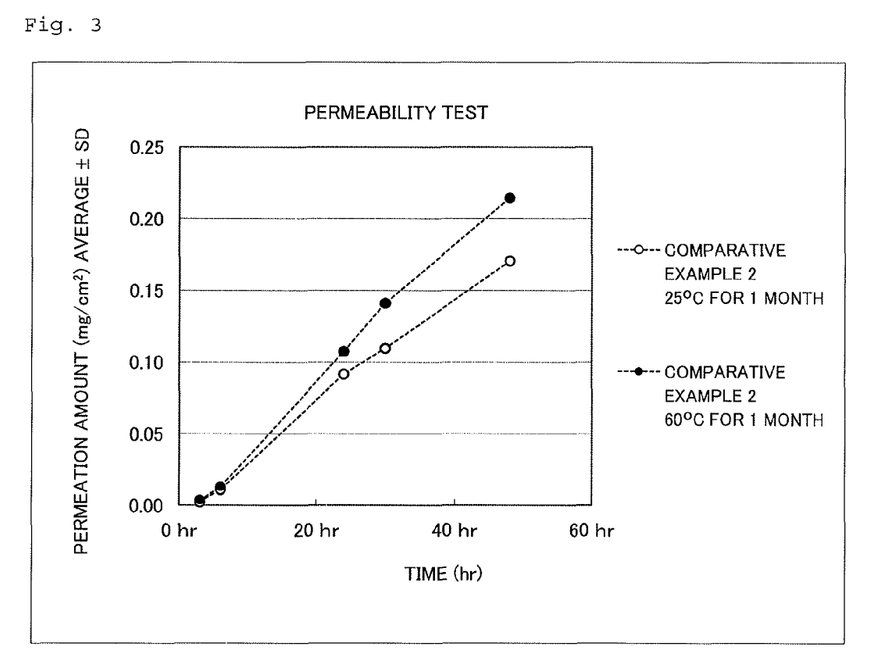
FIG. 3 is a graph showing the results of a permeability test performed on patches of Comparative Example 2 stored at 25° C. or 60° C. for one month.

Each of the medicated layers that had been formed on the release liner in Examples 1 and 3 and Comparative Example 1 but had not been integrally superposed on the PET films was removed from the release liner immediately after production. Then the medicated layer was cut into three square sheets of side 2 cm to obtain observation samples. Next, the observation samples were observed under a polarizing microscope at a magnification of 100×, and photographs were taken. The observation samples were wrapped and sealed with aluminum wrapping materials and stored in temperature atmospheres of 25° C., 40° C., and 60° C. After one month, each observation sample was removed, and the same observation area as that observed immediately after production was immediately observed and photographed, and the crystallized states of clonidine were compared. The results are shown in TABLE 1.

solution on the lower side of the skin was collected 3, 6, 24, 30, and 48 hours after the test piece was applied to the skin, and the concentration of clonidine was measured by HPLC. Then the permeation amount of clonidine per unit area of the test piece [Q (mg/cm$^2$)] determined from the clonidine concentration [N (mg/mL)] and the amount of the receptor solution [W (mL)] was computed at each time point using the formula: Q (mg/cm$^2$)=N (mg/mL)×W (mL)/3 (cm$^2$), and the determined value was used as a cumulative skin permeation amount. When the permeation amounts of clonidine were computed, since the receptor solution had been collected before the computation, the permeation amounts were corrected on the basis of the amount of the receptor solution collected. The results for Examples 2 and 4 are shown in FIG. 1, the results for Example 3 are shown in FIG. 2, and the results for Comparative Example 2 are shown in FIG. 3.

In Examples 2, 4, and 3, no or a very small change in the clonidine permeation amount due to storage temperature change was found. However, in Comparative Example 2, a significant change in the clonidine permeation amount due to storage temperature change was found.

Therefore, it was confirmed that, in the medicated layer included in each patch of the present invention, the stability of the absorption performance against temperature change during storage was improved.

TABLE 1

| STORAGE CONDITION | EXAMPLE 1 | EXAMPLE 3 | COMPARATIVE EXAMPLE 1 |
|---|---|---|---|
| IMMEDIATELY AFTER PRODUCTION | WELL-DEFINED CRYSTALS PRECIPITATED OVER ENTIRE SURFACE | WELL-DEFINED CRYSTALS PRECIPITATED OVER ENTIRE SURFACE | CRYSTALS WITH BLURRED OUTLINES PRECIPITATED OVER ENTIRE SURFACE |
| 25° C. FOR 1 MONTH | NO CHANGE | NO CHANGE | CRYSTAL GROWTH WAS OBSERVED |
| 40° C. FOR 1 MONTH | NO CHANGE | VERY SMALL AMOUNT OF CRYSTALS DISAPPEARED | DISAPPEARANCE OF CRYSTALS WAS OBVIOUS |
| 60° C. FOR 1 MONTH | VERY SMALL AMOUNT OF CRYSTALS DISAPPEARED | VERY SMALL AMOUNT OF CRYSTALS DISAPPEARED | DISAPPEARANCE OF CRYSTALS WAS OBVIOUS |

The crystalline forms of clonidine in the medicated layers in Examples 1 and 3 immediately after production were different from that in Comparative Example 1. In Examples 1 and 3, only a very small amount of clonidine crystals disappeared even after storage at 60° C. for one month. However, in Comparative Example 1, the disappearance of clonidine crystals was obvious. In Examples 1 and 3, the differences in changes in the crystallized state of clonidine due to the differences in storage temperature were very small. However, in Comparative Example 1, the changes in the crystallized state of clonidine were significantly different at different storage temperatures. Therefore, it was confirmed that, in the medicated layer included in each patch of the present invention, the change in the crystallized state of clonidine due to temperature change during storage was small.

3. Hairless Mouse Skin Permeability Test

Figure 4:
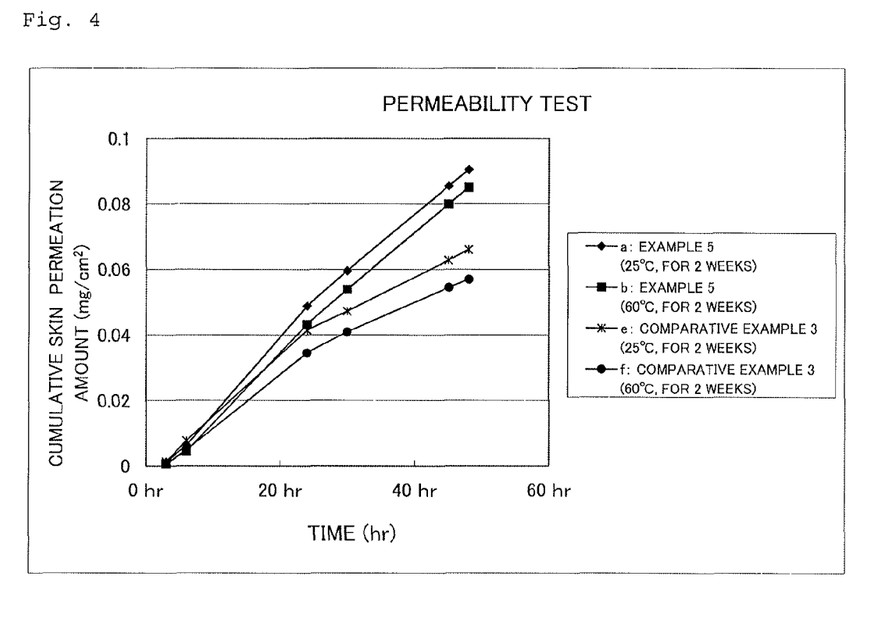
FIG. 4 is a graph showing the results of a permeability test performed on patches of Example 5 and Comparative Example 3 stored at 25° C. or 60° C. for two weeks.
Figure 5:
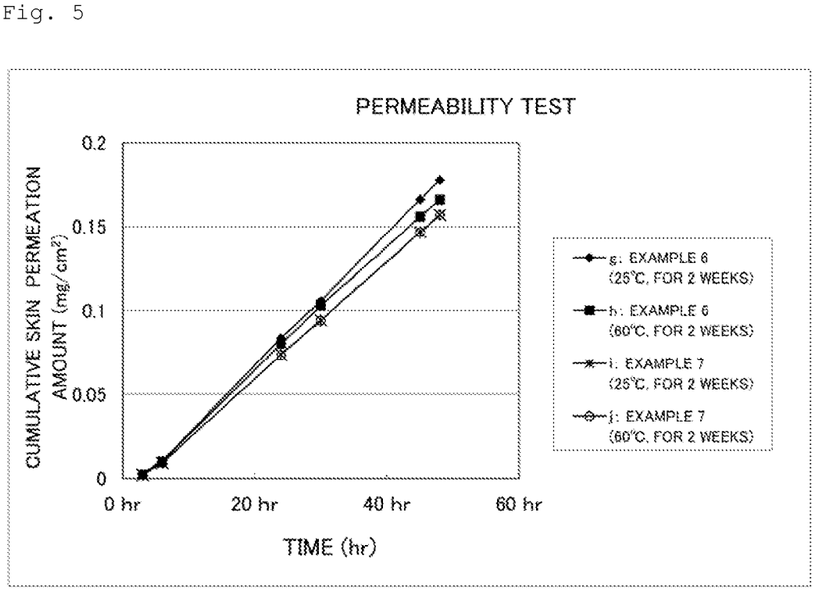
FIG. 5 is a graph showing the results of a permeability test performed on patches of Examples 6 and 7 stored at 25° C. or 60° C. for two weeks.
Figure 6:
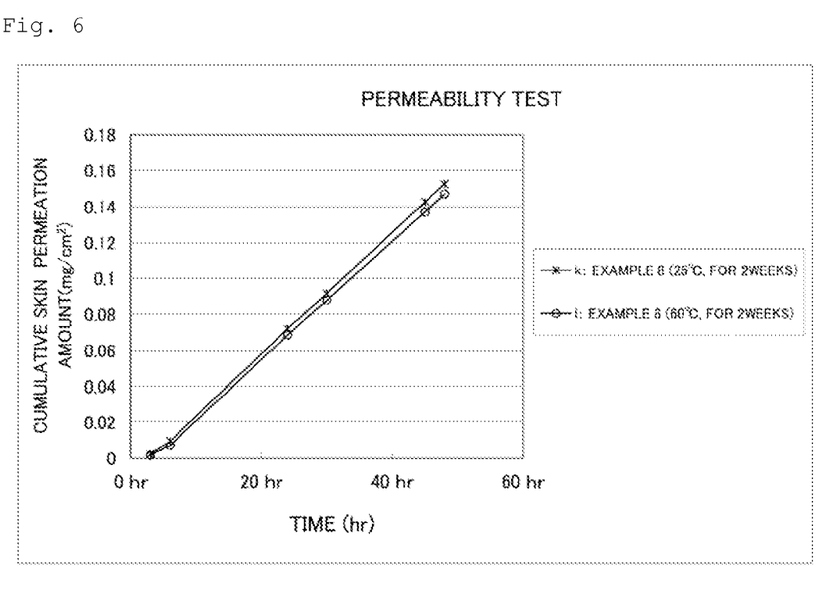
FIG. 6 is a graph showing the results of a permeability test performed on patches of Example 8 stored at 25° C. or 60° C. for two weeks.

After each of the patches in Examples 2, 3, and 4 and Comparative Example 2 was stored at 25° C. for one month or at 60° C. for one month, a rounded square test piece of side 1.8 cm (application area: 3 cm$^2$) was cut from the patch. Dorsal skin removed from a hairless mouse (male, 8 weeks old) was fixed on a Franz diffusion cell maintained at 37° C., and the test piece with the release liner removed was applied to the upper end of the skin through the adhesive layer of the test piece. A physiological saline solution with its pH adjusted to 7.2 was used as a receptor solution, and the lower end of the skin was immersed in the receptor solution. The receptor After each of the patches in Examples 5 to 8 and Comparative Example 3 was stored at 25° C. for two weeks or at 60° C. for two weeks, a rounded square test piece of side 1.8 cm (application area: 3 cm$^2$) was cut from the patch. Dorsal skin removed from a hairless mouse (male, 8 weeks old) was fixed on a Franz diffusion cell maintained at 37° C., and the test piece with the release liner removed was applied to the upper end of the skin through the adhesive layer of the test piece. A physiological saline solution with its pH adjusted to 7.2 was used as a receptor solution, and the lower end of the skin was immersed in the receptor solution. The receptor solution on the lower side of the skin was collected 20, 40, and 60 hours after the test piece was applied to the skin, and the concentration of clonidine was measured by HPLC. Then the permeation amount of clonidine per unit area of the test piece [Q (mg/cm$^2$)] determined from the clonidine concentration [N (mg/mL)] and the amount of the receptor solution [W (mL)] was computed at each time point using the formula: Q (mg/cm$^2$)=N (mg/mL)×W (mL)/3(cm$^2$), and the determined value was used as a cumulative skin permeation amount. When the permeation amounts of clonidine were computed, since the receptor solution had been collected before the computation, the permeation amounts were corrected on the basis of the amount of the receptor solution collected. The results for Example 5 and Comparative Example 3 are shown in FIG. 4, the results for Examples 6 and 7 are shown in FIG. 5, and the results for Example 8 are shown in FIG. 6.

Figure 7:
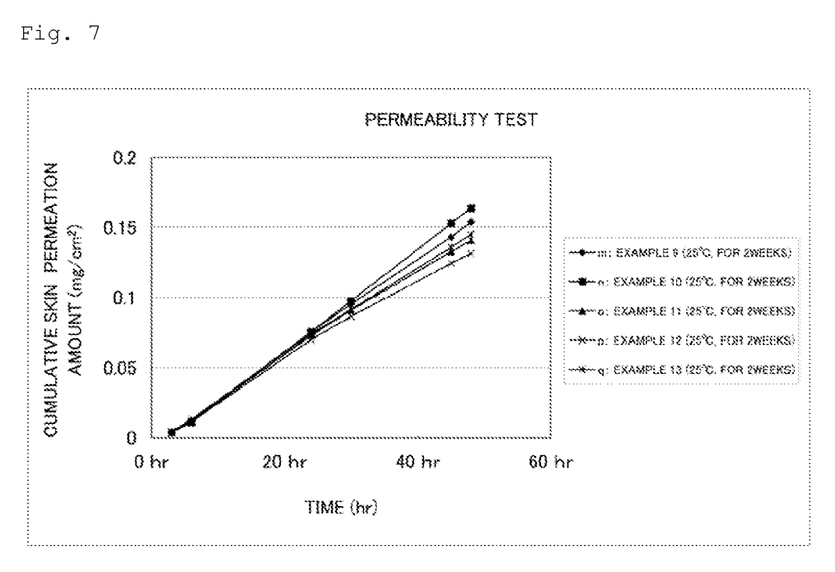
FIG. 7 is a graph showing the results of a permeability test performed on patches of Examples 9 to 13 stored at 25° C. for two weeks.

After each of the patches in Examples 9 to 13 was stored at 25° C. for two weeks, a rounded square test piece of side 1.8 cm (application area: 3 cm²) was cut from the patch. Dorsal skin removed from a hairless mouse (male, 8 weeks old) was fixed on a Franz diffusion cell maintained at 37° C., and the test piece with the release liner removed was applied to the upper end of the skin through the adhesive layer of the test piece. A physiological saline solution with its pH adjusted to 7.2 was used as a receptor solution, and the lower end of the skin was immersed in the receptor solution. The receptor solution on the lower side of the skin was collected 20, 40, and 60 hours after the test piece was applied to the skin, and the concentration of clonidine was measured by HPLC. Then the permeation amount of clonidine per unit area of the test piece [Q (mg/cm²)] determined from the clonidine concentration [N (mg/mL)] and the amount of the receptor solution [W (mL)] was computed at each time point using the formula: Q (mg/cm²)=N (mg/mL)×W (mL)/3(cm²), and the determined value was used as a cumulative skin permeation amount. When the permeation amounts of clonidine were computed, since the receptor solution had been collected before the computation, the permeation amounts were corrected on the basis of the amount of the receptor solution collected. The results for Examples 9 to 13 are shown in FIG. 7.

4. Evaluation of Adhesion Properties: Holding Power Test

For each of Examples 2 and 3 and Comparative Example 2, a flat rectangular test piece of 2.5 cm length×5.0 cm width was cut from the adhesive layer before superposition. One lateral edge of the test piece with the release liner removed was applied to a stainless steel test plate (application surface: 2.5×2.5 cm). A 2 kg rubber roller was moved back and forth one time on the test piece at a speed of 5 mm/second to compression-bond the test piece on the test plate, and the resultant test piece was left to stand at 40° C. for 20 minutes. A 300 g weight was attached to the other lateral edge of the test piece, and the test plate and the test piece were vertically erected while the weight was supported so that no load was applied to the test piece. Then the support of the weight was released to apply the load of the weight to the test piece. The time from the release of the support of the weight until the test piece fell off the test plate was measured. When the test piece did not fall off even after 60 minutes, the distance (mm) of the displacement of the test piece was measured. The results are shown in TABLE 2.

TABLE 2

| ADHESIVE LAYER | EXAMPLE 2 | EXAMPLE 3 | COMPARATIVE EXAMPLE 2 |
|---|---|---|---|
| HOLDING POWER (MINUTES) | OVER 6 (DID NOT FALL OFF) | OVER 60 (DID NOT FALL OFF) | 5 |
| DISPLACEMENT (mm) | 4 | 15 | — |

In each of the test pieces in Examples 2 and 3, the falling of the weight was not observed even after 60 minutes, and the weight was displaced only slightly. However, in the test piece in Comparative Example 2, the weight fell off in a short time. Therefore, it was confirmed that, in each patch of the present invention, the cohesion of the plaster was high and the adhesion of the patch was good.

5. Evaluation of Adhesion Properties: Ball Tack Test

For each of Examples 2 and 3 and Comparative Example 2, a rectangular test piece of 3 cm length×4 cm width was cut from the adhesive layer before superposition, and the release liner was removed from the test piece. Then the test piece was secured to a 30° inclined surface of a ball tack tester such that only the lateral middle section (3 cm width×3 cm length) of the adhesive layer was exposed. A steel ball conforming to JIS Z0237 was rolled from a position upwardly spaced 10 cm apart from the upper edge of the exposed adhesive layer of the test piece along the inclined surface, and whether or not the steel ball stopped on the test piece was observed. When the steel ball did not stop on the test piece and passed through the test piece, a smaller steel ball was rolled in the manner described above. The above procedure was repeated to measure the size of the smallest one of the steel balls that stopped on the test piece. The results are shown in TABLE 3. The larger the number of the steel ball, the larger the steel ball.

TABLE 3

| ADHESIVE LAYER | EXAMPLE 2 | EXAMPLE 3 | COMPARATIVE EXAMPLE 2 |
|---|---|---|---|
| STEEL BALL NUMBER | 6 | 6 | 7 |

The sizes of the steel balls that stopped on the test pieces in Examples 2 and 3 were smaller than that for the test piece in Comparative Example 2. However, the test pieces in Examples 2 and 3 were found to have sufficient tackiness. Therefore, it was confirmed that the adhesion of each patch of the present invention bore comparison with that of the patch in Comparative Example 2.

TABLE 4

| | | EXAMPLE 1 | EXAMPLE 2 | EXAMPLE 3 | EXAMPLE 4 | EXAMPLE 5 | EXAMPLE 6 |
|---|---|---|---|---|---|---|---|
| MEDICATED LAYER [% BY WEIGHT] | CLONIDINE | 13 | 13 | 13 | 13 | 13 | 13 |
| | MACROMOLECULAR BASE (A) | 28 | 28 | 29 | 28 | 40 | 30 |
| | MACROMOLECULAR BASE (B) | 12 | 12 | 3 | 12 | 11 | 5 |
| | LIQUID ADDITIVE | 39 | 39 | 47 | 39 | 28 | 44 |
| | LIGHT SILICIC ACID ANHYDRIDE | 8 | 8 | 8 | 8 | 8 | 8 |
| | WEIGHT RATIO [LIQUID ADDITIVE/ MACROMOLECULAR BASE (A)] | 1.39 | 1.39 | 1.62 | 1.39 | 0.7 | 1.47 |

TABLE 4-continued

|  |  |  |  |  |  |  |  |
|---|---|---|---|---|---|---|---|
| ADHESIVE LAYER [% BY WEIGHT] | CLONIDINE | — | 3 | 3 | 1 | 1 | 3 |
|  | MACROMOLECULAR BASE (A) | — | 35 | 39 | 36 | 36 | 30 |
|  | MACROMOLECULAR BASE (B) | — | 15 | 3 | 15 | 15 | 12 |
|  | LIQUID ADDITIVE | — | 38 | 47 | 39 | 39 | 47 |
|  | LIGHT SILICIC ACID ANHYDRIDE | — | 9 | 8 | 9 | 9 | 8 |
|  | WEIGHT RATIO [LIQUID ADDITIVE/ MACROMOLECULAR BASE (A)] | — | 1.09 | 1.21 | 1.08 | 1.08 | 1.57 |
|  | THICKNESS [μm] | — | 50 | 50 | 50 | 50 | 50 |

| | | EXAMPLE 7 | EXAMPLE 8 | EXAMPLE 9 | EXAMPLE 10 |
|---|---|---|---|---|---|
| MEDICATED LAYER [% BY WEIGHT] | CLONIDINE | 13 | 13 | 10 | 10 |
|  | MACROMOLECULAR BASE (A) | 30 | 30 | 30 | 30 |
|  | MACROMOLECULAR BASE (B) | 5 | 5 | 5 | 5 |
|  | LIQUID ADDITIVE | 44 | 44 | 47 | 47 |
|  | LIGHT SILICIC ACID ANHYDRIDE | 8 | 8 | 8 | 8 |
|  | WEIGHT RATIO [LIQUID ADDITIVE/ MACROMOLECULAR BASE (A)] | 1.47 | 1.47 | 1.57 | 1.57 |
| ADHESIVE LAYER [% BY WEIGHT] | CLONIDINE | 2 | 1 | 1 | 1 |
|  | MACROMOLECULAR BASE (A) | 30 | 30 | 30 | 30 |
|  | MACROMOLECULAR BASE (B) | 13 | 14 | 14 | 14 |
|  | LIQUID ADDITIVE | 47 | 47 | 47 | 47 |
|  | LIGHT SILICIC ACID ANHYDRIDE | 8 | 8 | 8 | 8 |
|  | WEIGHT RATIO [LIQUID ADDITIVE/ MACROMOLECULAR BASE (A)] | 1.57 | 1.57 | 1.57 | 1.57 |
|  | THICKNESS [μm] | 50 | 50 | 50 | 30 |

TABLE 5

| | | EXAMPLE 11 | EXAMPLE 12 | EXAMPLE 13 | COMPARATIVE EXAMPLE 1 | COMPARATIVE EXAMPLE 2 | COMPARATIVE EXAMPLE 3 |
|---|---|---|---|---|---|---|---|
| MEDICATED LAYER [% BY WEIGHT] | CLONIDINE | 10 | 10 | 10 | 13 | 13 | 13 |
|  | MACROMOLECULAR BASE (A) | 30 | 30 | 30 | 20 | 20 | 49 |
|  | MACROMOLECULAR BASE (B) | 5 | 5 | 5 | 12 | 12 | 30 |
|  | LIQUID ADDITIVE | 47 | 47 | 47 | 47 | 47 | 0 |
|  | LIGHT SILICIC ACID ANHYDRIDE | 8 | 8 | 8 | 8 | 8 | 8 |
|  | WEIGHT RATIO [LIQUID ADDITIVE/ MACROMOLECULAR BASE (A)] | 1.57 | 1.57 | 1.57 | 2.35 | 2.35 | 0 |
| ADHESIVE LAYER [% BY WEIGHT] | CLONIDINE | 1 | 1 | 1 | — | 3 | 1 |
|  | MACROMOLECULAR BASE (A) | 30 | 30 | 30 | — | 29 | 36 |
|  | MACROMOLECULAR BASE (B) | 14 | 14 | 14 | — | 12 | 15 |
|  | LIQUID ADDITIVE | 47 | 47 | 47 | — | 47 | 39 |
|  | LIGHT SILICIC ACID ANHYDRIDE | 8 | 8 | 8 | — | 9 | 9 |
|  | WEIGHT RATIO [LIQUID ADDITIVE/ MACROMOLECULAR BASE (A)] | 1.57 | 1.57 | 1.57 | — | 1.62 | 1.08 |
|  | THICKNESS [μm] | 110 | 150 | 200 | — | 50 | 50 |

INDUSTRIAL APPLICABILITY

According to the present invention, a patch in which the behavior of dissolution-deposition of clonidine present in a crystallized state in the medicated layer due to temperature change during storage is stabilized can be provided. The temperature (quality) control of such a patch during distribution and storage can be facilitated.

The invention claimed is:

1. A patch comprising:
   a backing; and
   a medicated layer integrally superposed on one surface of the backing,
   wherein the medicated layer comprises:
   5 to 30% by weight of clonidine including clonidine in a crystallized state;
   25 to 90% by weight of a macromolecular base (A) having a viscosity-average molecular weight of 800,000 or larger; and
   5 to 60% by weight of a liquid additive capable of dissolving the clonidine,
   wherein a weight ratio of the liquid additive to the macromolecular base (A) [the liquid additive/the macromolecular base (A)] in the medicated layer is 0.1 to 1.7.

2. The patch according to claim 1, wherein the medicated layer comprises 25 to 85% by weight of the macromolecular base (A).

3. The patch according to claim 2, wherein the medicated layer further comprises 1 to 69% by weight of a macromolecular base (B) having a viscosity-average molecular weight of 10,000 or larger and less than 800,000.

4. The patch according to claim 1, wherein the macromolecular base (A) comprises a rubber-based adhesive or an alkyl (meth)acrylate copolymer having no polar functional group.

5. The patch according to claim 1, wherein the macromolecular base (A) comprises polyisobutylene.

6. The patch according to claim 1, wherein the liquid additive comprises liquid paraffin.

7. The patch according to claim 1, further comprising an adhesive layer being integrally superposed on one surface of the medicated layer,
    wherein the adhesive layer comprises:
        0.5 to 3% by weight of clonidine,
        25 to 90% by weight of a macromolecular base (A) having a viscosity-average molecular weight of 800,000 or larger, and
        5 to 60% by weight of a liquid additive capable of dissolving the clonidine,
    wherein a weight ratio of the liquid additive to the macromolecular base (A) [the liquid additive/the macromolecular base (A)] in the adhesive layer is 0.1 to 2.0.

8. The patch according to claim 7, wherein the adhesive layer further comprises 1 to 25% by weight of a macromolecular base (B) having a viscosity-average molecular weight of 10,000 or larger and less than 800,000.

9. The patch according to claim 7, further comprising a control layer interposed between the medicated layer and the adhesive layer,
    wherein the control layer comprises a porous film having a large number of through holes extending between opposite sides of the porous film and formed of a polyolefin-based resin, and a liquid additive which the through holes are filled with.

* * * * *